United States Patent [19]

McKenna et al.

[11] Patent Number: 5,783,714

[45] Date of Patent: Jul. 21, 1998

[54] MANUFACTURE OF ALIPHATIC CALCIUM CARBOXYLATE

[76] Inventors: Arthur L. McKenna, 6447 Golfview La., Palos Heights, Ill. 60463; Oscar Knott, 10353 S. Nashville, Chicago Ridge, Ill. 60415; Nina M. McConnell, 2450 Forest Dr., Woodridge, Ill. 60517

[21] Appl. No.: 818,412

[22] Filed: Mar. 17, 1997

Related U.S. Application Data

[63] Continuation of Ser. No. 363,701, Dec. 23, 1994, abandoned.

[51] Int. Cl.$^6$ .................................................. C07C 51/00
[52] U.S. Cl. ............................................ 554/156; 252/56 R
[58] Field of Search ......................... 554/156; 252/56 R

[56] References Cited

PUBLICATIONS

Chemical Abstracs 71:72600, 1969.
Chemical Aabstracts 78:18670, 1972.
Chemical Abstracs 80:5502, 1972.
Chemical Abstracts 82:61772, 1974.
Chemical Abstracts 84:138223, 1975.
Chemical Absracs 105:229667, 1986.
Chemical Abstract 114:8456, 1991.

*Primary Examiner*—Gary Geist
*Assistant Examiner*—Deborah D. Carr
*Attorney, Agent, or Firm*—Lockwood, Alex, FitzGibbon & Cummings

[57] ABSTRACT

A process is disclosed for manufacturing a substantially grit-free calcium salt of an aliphatic carboxylic acid having twelve to twenty-two carbon atoms comprising the steps of (1) conveying into a mixing zone at least one aliphatic carboxylic acid having twelve to twenty-two carbon atoms and a calcium hydroxide product having a maximum particle size of 22 microns, (2) applying heat as necessary, (3) mixing until the reaction has progressed to the desired end point, and (4) discharging calcium carboxylate salt from the mixing zone.

The disclosed process affords a novel calcium salt of a carboxylic acid such as one comprising a calcium stearate substantially free of grit, characterized by a melting range from 131° C. to 159° C., an ash content in the range from 9 to 12% by weight as calcuim oxide, a free fatty acid content not exceeding 1% by weight, a water soluble salt content in the range from 0.001% to 0.1% by weight, and an apparent density in the range from 15 to 25 pounds per cubic foot.

The disclosed process further affords a novel calcium salt of a carboxylic acid substantially free of grit which can be incorporated in polypropylene without excessive extrusion screen pack pressure buildup.

23 Claims, No Drawings

MANUFACTURE OF ALIPHATIC CALCIUM CARBOXYLATE

This application is a continuation of application Ser. No. 08/363,701, filed Dec. 23, 1994, now abandoned.

This invention relates to novel calcium soaps such as calcium stearate and other calcium salts of aliphatic carboxylic acids having from 12 to 22 carbon atoms that are substantially free of grit, and to a process for the manufacture thereof.

BACKGROUND OF THE INVENTION

Calcium soaps such as calcium stearates are useful materials in industry and agriculture. They have been used as waterproofing agents, as additives in plastics processing for their thickening, lubricating and acid scavenging properties, and as a high energy feed supplement for cattle.

The chemistry of making calcium soaps can be described as deceptively simple, "merely" consisting of classical acid-base neutralization and double-decomposition reactions. Thus, the synthesis of a calcium stearate by neutralization can be represented by the reaction equation $$2\ RCO_2H + Ca(OH)_2 \rightarrow (RCO_2)_2Ca + H_2O$$

in which R represents the aliphatic hydrocarbon group (e.g. C17H35) of stearic acid, while the preparation by double decomposition can be represented by the reaction equations $$2\ RCO_2H + 2\ NaOH \rightarrow 2\ RCO_2Na + 2\ H_2O$$

$$2\ RCO_2Na + CaCl_2 \rightarrow (RCO_2)_2Ca + 2\ NaCl$$

The equations, however, barely hint at the problems that must be solved in order to convert the classical chemistry into economical manufacture of high quality calcium soaps, and they totally ignore certain properties of the resulting products that can affect their performance in actual use. In particular, these neutralization and double decomposition reactions do not proceed instantaneously and quantitatively to completion under all conditions. The usual practice, therefore, is to prepare calcium salts with an excess of the calcium base over the fatty acid when it is considered important to consume the fatty acid as completely as possible, or with an excess of fatty acid over the metal base when unconverted metal base is objectionable. The various preparations differ in their properties; one or another may be preferred, depending on the properties required by particular uses.

The different preparations also differ in their costs; the double decomposition process is generally deemed to be more labor intensive and less efficient in terms of quantity produced in equipment of a given size per unit time, as compared to the neutralization process. The double decomposition method generally yields extremely fine, bulky and soft powders, while the direct neutralization products can be ground to a range of particle sizes but not as fine or soft as the precipitated products. Moreover, it has been difficult to obtain products of the direct neutralization free of hard particles or grit, and traditional processing methods such as grinding and screening have not been able to eliminate such grit.

Accordingly, the art has long sought to improve the quality of calcium soaps produced by the direct neutralization reaction in order to enable such products to be successfully used in certain demanding applications, particularly, in plastics processing, where only calcium soaps produced by double decomposition have been considered suitable.

For consideration of some details that guide the selection of particular kinds of calcium soaps in such plastics systems as polyester bulk molding compound and sheet molding compound, polyolefins such as polyethylene and polypropylene, and polyvinyl chloride formulations, the chapter "Fatty Acids and their Derivatives" by D. Dieckmann in "Plastics Additives and Modifiers Handbook" (J. Edenbaum, editor, Van Nostrand Reinhold 1992) pages 858–867 can be consulted.

J. Freeland U.S. Pat. No. 3,376,327 of Apr. 2 1968 disclosed a neutralization process for calcium and magnesium soaps comprising the addition with agitation of calcium hydroxide or other alkaline earth compound to selected fatty acid heated to 90° to 150° F. (32°–65° C.) but at least above the melting temperature of the fatty acid, the alkaline earth compound being comminuted to at least through 100 mesh (equivalent to 150 microns), preferably 200 mesh (75 microns). The relative amount of the alkaline earth compound used is such as to be from 1.25 to 5 equivalent weights of the fatty acid, so that the composition must contain an excess of the alkaline earth compound. The excess of the alkaline earth compound remains in the composition and is stated to contribute to the solidity of the final composition and to the remarkable behavior during processing whereby the temperature suddenly starts to rise while the admixture is still fluid.

R. Lally et al. U.S. Pat. No. 3,476,786 of Nov. 4, 1969 disclosed that heavy metal soaps in a fine anhydrous powdery state can be formed by the direct inter-reaction of a solid anhydrous metal component selected from the group consisting of polyvalent metals, oxides of polyvalent metals, hydroxides of polyvalent metals, carbonates of polyvalent metals and mixtures thereof with at least one solid anhydrous fatty acid containing from 10 to 22 carbon atoms in the presence of particular catalysts and in the absence of water at ambient temperatures by the continual subdivision of the solid particles by various methods of grinding. Continuous subdivision of the particles by means of grinding should take place for at least 10 minutes, preferably from about 15 minutes to about 30 hours or longer, although in most cases no additional benefits result from using grinding times above ten hours. Catalysts are stated to be anhydrous and include any anhydrous water-soluble inorganic basic salt, any anhydrous water-soluble inorganic acid salt, any water-soluble organic amine base and mixtures thereof. Nothing is disclosed about the particle size of metal compounds to be reacted. Disclosure of reacting proportions is confined to working examples, reactions being disclosed of 800 parts by weight of dry powdered stearic acid being ground with 180 parts by weight of anhydrous powdered calcium hydroxide, either without catalyst or with 16 parts by weight of anhydrous ammonium carbonate catalyst. These reactions resulted in products containing 37% and 19% free fatty acid respectively, thus indicating incomplete consumption of the fatty acid in spite of the use of the catalyst and considerable excess calcium hydroxide.

L. Scott et al. U.S. Pat. No. 3,803,188 of Apr. 9, 1974 disclosed a process of preparing metallic soaps of Group II of the Periodic Table by dispersing the finely ground metal oxides of Group II in molten higher fatty acids and mixing well therein from 3.5 to 40 mole-equivalents of water per mole-equivalent of fatty acid, preferably from 5 to 40 mole-equivalents of water for most of the oxides. The use of anionic, cationic and nonionic surfactants as catalysts for the reaction is also disclosed. In so doing, the reaction velocity is increased so that a shorter reaction time is required. The metal oxide is stated to be finely ground; the finer the particle size of the metallic oxide and the better the dispersion in the fatty acid, the more rapid and uniform is the reaction, but no data on the fineness of any oxide used is given. The reaction is initiated at a temperature between 55° and 135° C. and the proportion of water within the disclosed range is selected so as to always maintain the temperatures of the reaction mixture below the melting point of the soap being prepared; when the temperature of the initial reaction is raised to obtain shorter induction and reaction time, the ratio of water to fatty acid must also be raised to provide sufficient cooling to prevent fusion of the product. It is also disclosed that while the reaction proceeds very rapidly at mole-equivalent ratios 2 to 1 and above of metal oxide to fatty acid, ratios as low as 0.5 to 1 can be employed, with longer reaction times required with some oxides in order to obtain a product with a low free fatty acid at low mole-equivalent ratios of the order of 1:1 and lower. In all preparations of calcium soaps included in the disclosure, the mole-equivalent ratio of calcium oxide to fatty acid is 1.2 or higher.

The insufficiency of these disclosures in overcoming continuing difficulties in the manufacture of calcium carboxylates by direct neutralization can be seen from renewed interest in the double decomposition method. Thus, Youkinawa et al. U.S. Pat. No. 5,175,322 of Dec. 20, 1992 disclosed a continuous process for preparing a metallic soap such as calcium stearate by double decomposition, in which an aqueous solution of alkali soap and an inorganic salt in the form of powder or aqueous solution are separately fed directly on the surface of the rotating impeller of a mixer and the produced metallic soap slurry is immediately and continuously discharged from the mixer. The equivalent ratio of inorganic metal salt to alkali soap usually ranges from 0.95 to 1.05 and for the production of calcium stearate in particular it is in the range from 1.00 to 1.05, preferably from 1.00 to 1.02. If it is less than 1.00 the amount of residual alkali soap which is hardly removed in the subsequent washing step increases. Preparations of calcium stearate from aqueous solutions of sodium stearate and of calcium chloride are disclosed in which the equivalent ratio of calcium chloride to sodium stearate was 1.02, the water soluble content of the resulting calcium stearate ranged from 0.18% to 0.23%, and the average particle size of the product ranged from 4.9 to 5.3 microns. No other properties are given.

In more recent efforts to improve the direct neutralization process, Carduck et al. U.S. Pat. No. 5,185,457 of Feb. 9, 1993 disclosed a continuous process for producing metal soaps by subjecting a molten fatty acid to a rotation in one direction by mechanical transport and transporting the fatty acid into a reaction zone of a tube reactor, and subjecting a metal compound such as a metal oxide or hydroxide to a rotation by mechanical transport in a direction opposite to the direction of rotation of the fatty acid and transporting the metal compound into the reaction zone in the vicinity of the axis of rotation of the fatty acid in the reaction zone to form a mixture, and reacting the mixture in the reaction for 0.50 to 50 seconds while being mechanically transported through the reaction zone with rotation, and recovering the soap at the exit from the reaction zone. While it is disclosed that the basic components are present preferably in a quantity of 1 to 3 equivalents of the metal compounds per mole fatty acid, the only disclosure of a reaction with calcium hydroxide shows the continuous charge of 91 kg/hour calcium hydroxide with 413 kg/hour soybean fatty acid with acid value of 186 mg KOH per gram, for a ratio of 1.67 mole equivalent calcium hydroxide to fatty acid resulting in a basic calcium soap of soybean oil fatty acid suitable as feed additive for ruminants.

M. Lajoie U.S. Pat. No. 5,212,325 of May 18 and U.S. Pat. No. 5,250,714 of Oct. 5, 1993 has disclosed production of fatty acid metal salts for ruminant animal feed supplement, in which an admixture is formed of reactive ingredients comprising C14–C22 fatty acid, basic alkaline earth metal compound in proportions of 0.8 to 1.2 equivalents per equivalent of fatty acid, a quantity of basic alkali metal compound which provides an alkaline earth metal to alkali metal atomic ratio between about 2:1 and 20:1, and about 10 to 50 weight percent of an aqueous medium, based on the weight of fatty acid, and the salt product is recovered after completion of the exothermic salt forming reaction. The fatty acid salt product is described as a friable solid which comprises both a fatty acid salt of an alkaline earth metal and a basic alkali metal compound wherein the atomic ratio of alkaline earth metal is between about 2:1 and 20:1. It is disclosed that the alkaline earth metal component preferably has a particle size which passes a 150 micron mesh screen. In each preparation of a calcium salt disclosed by Lajoie, the combined calcium and alkali metal equivalents are in excess of the equivalents of fatty acid.

W. Wuest et al. U.S. Pat. No. 5,274,144 of Dec. 28, 1993 disclosed a process for the production of metal soaps from liquid fatty acids with solid metals oxides and/or metal hydroxides, in which a stream of the liquid phase of fatty acid kept under reduced pressure in the reactor is run off into an external premixing zone and contacted there with a solid metal oxide and/or metal hydroxide in a solid/liquid reaction, and the reaction product formed is returned to the reactor via a following intensive mixer and the water of neutralization formed is continuously removed from the reactor via the gas phase. The solid metal oxide and/or hydroxide are introduced into the fatty acid melt in such a way that the particle size of the agglomerate formed is below 10 microns and the acid values of the metal soaps formed are between 0.1 and 30 and preferable between 0.5 and 10. Nothing is disclosed as to the particle size or condition of a metal oxide and/or hydroxide as supplied to the reaction. For each reaction of calcium hydroxide with a fatty acid disclosed, it is stated that an acid value of 5 to 10 for the finished product was required, but nothing is stated as to what acid value was obtained.

M. Lajoie Chemical Abstracts 121: 133540q, Sep. 12, 1994 (Abstract of PCT International Application 94 13615, published Jun. 23, 1994) disclosed the preparation of mixed calcium salts of fatty acids containing 25–50% oleic acid and 2–20% linoleic acid along with palmitic acid, stearic acid, and lauric acid, which contain little or no free acid or fatty acid glyceride, which can function as a rumen bypass animal feed supplement.

It is evident that numerous processes have been disclosed that differ in the properties of the resulting products and in their cost. Still needed is a low cost process affording a versatile calcium soap meeting the most demanding requirements, such as the substantial absence of grit and the ability to pass increasingly finer screen packs with out clogging or excessive pressure buildup when incorporated into polyethylene and polypropylene. It has been believed that the latter performance requirement correlates with the lowest possible contents of both free fatty acid and unconsumed calcium base which have only been available in products of the labor intensive and high cost double decomposition process.

SUMMARY OF THE INVENTION

In accordance with this invention, a direct neutralization process for manufacturing a substantially grit-free calcium salt of an aliphatic carboxylic acid having twelve to twenty-two carbon atoms comprises the steps of (1) conveying into a mixing zone at least one aliphatic carboxylic acid having twelve to twenty-two carbon atoms and a calcium hydroxide product having a maximum particle size of 22 microns, (2) applying heat as necessary, (3) mixing until the reaction has progressed to the desired end point, and (4) discharging calcium carboxylate salt from the mixing zone.

The process of this invention affords a novel calcium salt of a carboxylic acid such as one comprising a calcium stearate substantially free of grit characterized by a melting range from 131° to 159° C., an ash content in the range from 9% to 12% by weight as calcium oxide, a free fatty acid content not exceeding 1% by weight, a water soluble salt content in the range from 0.001% to 0.1% by weight, and an apparent density in the range from 15 to 25 pounds per cubic foot.

The process of this invention further affords a novel calcium salt of a carboxylic acid such as calcium stearate substantially free of grit which can be dissolved in hot decalin to give a solution that has at most a slight visible haze and transmission at 650 nm of a 3% w/w solution measured at 130° C. of at least 90%, and which can be incorporated in polyolefin plastics with minimal extrusion screen pack pressure buildup.

DESCRIPTION OF PREFERRED EMBODIMENTS

All aliphatic carboxylic acids having twelve to twenty-two carbon atoms can be used in the manufacture of calcium carboxylates according to this invention. Preferred are acids having a single carboxyl group attached to a straight chain saturated hydrocarbyl group. Mixtures of acids can be used, including particularly commercial grades of fatty acids that are actually mixtures of two or more acids. Particularly, preferred acids include behenic acid, lauric acid, myristic acid, palmitic acid, and stearic acid. Filtered, grit-free acids are used for best results.

As used herein, stearic acid or calcium stearate refer, respectively, to mixtures or calcium salts of commercially available stearic acid stocks and the term stearic acid is not meant to be limited to pure n-octadecanoic acid, although such acid is useful in the present invention. Commercially available "stearic acids" are complex mixtures of carboxylic acids, mostly C-18, C-16, with some C-14 and lesser amounts of other acids, ranging from C-6 to C-22. It will be appreciated that stearic acid and calcium stearate are used herein as exemplary materials and values provided for such materials, such as percentages by weight, melting range, etc. are representative values for such materials.

Calcium soaps that can be manufactured according to this invention include calcium behenate, calcium laurate, calcium myristate, calcium palmitate, and calcium stearate. When two or more aliphatic carboxylic acids are used, there can be manufactured mixed calcium carboxylate soaps such as calcium laurate-myristate or calcium behenate-stearate. Of course, mixtures of carboxylic acids derived from hydrogenation of natural ratios characteristic of natural sources can also be used and the calcium soaps manufactured from such mixtures will also be a mixed calcium carboxylate soap product.

In accordance with this invention, the calcium hydroxide raw material is a high surface to volume ratio lime, suitably having 97% of particles equal to or smaller than 11 micron average particle size and 100% equal to or smaller than 22 microns. Such lime when not commercially available can be obtained by a variety of techniques, including slurry attrition, grinding, or air classification of powder. High surface to volume ratio lime used in accordance with this invention must be protected from exposure to carbon dioxide which forms calcium carbonate on the surface and diminishes reactivity. For maximum effectiveness the carbonate content of the lime must not exceed 1.36% as calcium carbonate or 0.6% as carbon dioxide by weight.

The yield of calcium soap afforded by the process of this invention is substantially quantitative, and there are only trace (at most) by-products other than water formed in the neutralization reaction. Consequently, the proportions of calcium to carboxylic acid found in the product are governed by the proportions of calcium hydroxide and carboxylic acid starting material conveyed into the mixing zone according to this invention. Preferably, these proportions are in the range of 1.8 moles to 2.2 moles of carboxylic acid per mole of calcium hydroxide. More preferably these proportions are in the range of 1.96 moles to 2.01 moles of carboxylic acid per mole of calcium hydroxide to provide a calcium soap whose percent transmission at 650 nm of a 3% solution in decalin at 130° C. is at least 90%. When the carboxylic acid used is stearic acid, the relative proportions are preferably in the range from 13 parts by weight to 17 parts by weight of calcium hydroxide per 100 parts by weight of stearic acid.

A variety of conventional high shear reaction vessels provide effective mixing zones for carrying out the process of this invention as well as means for heating and cooling, such as coils or jackets for the introduction of steam, cooling water, or other suitable heat transfer fluids. Such mixers should have sufficient power and blade conformation to allow high shear mixing of viscous liquids and/or powders. Mixing in accordance with this invention is preferably provided at an agitation rate of 40 to 150 rpm.

Atmospheric, superatmospheric, and subatmospheric pressures can be applied in the process of this invention as desired. It is convenient to close the reaction vessel when all ingredients have been added and allow the pressure to rise to superatmospheric levels as the temperature increases to 100° C. and above. Near the end of the reaction, the pressure is reduced to less than or equal to ambient to remove residual water.

In accordance with this invention, calcium hydroxide having a maximum particle size of 22 microns is mixed with the carboxylic acid reaction at a temperature such that a good dispersion of the hydroxide in the acid is obtained before appreciable reaction takes place. When dispersion is obtained, heat is applied to initiate the reaction, which then continues exothermally until close to completion and can evolve much of the water by-product of the reaction in the form of steam. Heat is again applied to assist in completing the reaction and drying the product. For best results, the temperature is maintained in a range from 50° to 110° C. during the reaction.

The presence of water is believed to be helpful in carrying out the process of this invention especially in the early and latter stages of the reaction where the water by-product of the reaction is not sufficiently available to carry out its critical reaction initiation function. The amount of water is usually no more than necessary in order not to increase unduly the consumption of time and energy in drying the finished product. For example, when stearic acid is the selected carboxylic acid, water in a proportion of 2 to 10 parts by weight per 100 parts by weight of stearic acid is initially added.

A small amount of surfactant can be included in the reaction mixture, if desired, to assist in the dispersion of calcium hydroxide in the carboxylic acid. The relative proportion of surfactant when present is preferably 0.05 to 0.5% by weight based on the amount of carboxylic acid. The surfactant can be selected from among cationic, nonionic, anionic, and betaine-type or zwitterionic agents. A particularly preferred type of surfactant is an alkylaryl polyoxy carboxylate (See Witco Corporation Material Safety Data Sheet for Emcol® CNP-110 surfactant).

It has been found helpful in completing the reaction and assuring the consumption of the calcium hydroxide in accordance with this invention as fully as possible to add minor amounts of acetic acid. When acetic acid is so used, the relative proportion of acetic acid to carboxylic acid having from 12 to 22 carbon atoms is suitably one mole of the former for 18 to 280 moles of the latter, preferably one mole of the former for 80 to 170 moles of the latter. It is believed that acetic acid when so used is present at least in part in the product of the reaction in the form of calcium acetate. Accordingly, when the carboxylic used in the process is stearic acid and a minor amount of acetic acid is added, there result in accordance with this invention compositions that comprise a minor amount of calcium acetate and a major amount of calcium stearate, suitable in molar proportions of calcium acetate to calcium stearate ranging from 1:18 to 1:280, preferably from 1:80 to 1:170. Such compositions are particularly suitable as acid-acceptors and scavengers of halide catalyst residues in polyolefin plastics made with Ziegler-Natta and other transition metal based polymerization catalysts, including such polyolefins as ethylene homopolymer, propylene homopolymer, and copolymers of ethylene with at least one alpha-olefin having three to eight carbon atoms, including crystalline ethylene-propylene copolymers, rubbery ethylene-propylene copolymers, and copolymers of major amounts of ethylene with minor amounts of 1-butene, 1-hexene or 1-octene.

It has also been found helpful in completing the reaction and assuring the consumption of the calcium hydroxide in accordance with this invention as fully as possible to add minor amounts of a fatty triglyceride, preferably a saturated fatty triglyceride such as hydrogenated palm oil, hydrogenated tallow, and other readily available triglycerates. When a triglyceride is so used, the relative proportion by weight of triglyceride to carboxylic acid having from 12 to 22 carbon atoms ranges from 4:96 to 1:99. When the carboxylic used in the process is stearic acid and a minor amount of triglyceride is added, there result in accordance with this invention compositions that comprise a minor amount of triglyceride and a major amount of calcium stearate. Such compositions are particularly suitable as acid-acceptors and scavengers of halide catalyst residues in polyolefin plastics made with Ziegler-Natta and other transition metal polymerization catalysts as disclosed above.

To be suitable for use as acid-acceptor and scavenger in polyolefin plastics, a calcium soap must be substantially free of grit and contain not more than traces of unreacted calcium hydroxide. Such suitability can be demonstrated in several ways. One such test is where decalin at 125°–135° C. is used to prepare a 3% w/w solution whose transmission at 650 nm is read spectrophotometrically. For a suitable product, the transmission so determined is at least 90%.

An extrusion test with polypropylene can be carried out to provide an indication of the amount of particles non-meltable at 260° C. and extraneous impurities. A special fiber grade polypropylene without additives and with the least possible content of high molecular weight gels is used. Approximately 1000 grams of such polypropylene containing the desired level of calcium stearate, suitably 25000 parts per million for a test that exaggerates a potential problem or 500 to 5000 parts per million for a test that simulates industrial use levels, is extruded through a 325/200/100/60 mesh screen pack at 1000 rpm using a ¾ inch single-screw extruder filler with a 25/1 L/D screw at 260° C. As the polymer is passed through 0.049 square inch pores of a 325 mesh filter positioned in line at the end of the extruder barrel, the pores become blocked by impurities and gels causing the pressure behind the filter to rise proportionally. The extent of this pressure rise in relation to the amount of polymer extruded indicates the contamination level. (The contribution of gels in the polymer to the pressure rise can be determined by a control extrusion with polypropylene without any calcium soap). The lower the contamination, the more suitable the polymer is for use in fiber and film manufacturing. Percent pressure rise per pound is calculated as:

$$\frac{(\text{Final pressure in } psig - \text{initial pressure in } psig) \times 453.8 \times 100}{(\text{Initial pressure in } psig) \times (\text{sample weight in grams})}$$

For use in polyvinyl chloride plastics, calcium stearate substantially free of grit manufactured in accordance with this invention can be shown to be suitable by filtration of the previously noted decalin test solution through a 325 mesh screen where no retention should be observable. In a particular sensitive application, calcium stearate is included in a polyvinyl chloride solution topcoat applied to extruded polyvinyl chloride siding by knife blade coating, where any grit contained in the calcium stearate would score and damage the coating.

The following Examples are provided for purpose of illustration and are not intended to limit the scope of the invention as defined by the appended claims.

EXAMPLE 1

In a jacketed reaction vessel, one thousand parts of commercial stearic acid (average molecular weight 272–278) was melted and screened through 325 mesh to remove fibers and solid contaminants.

Calcium hydroxide (142 parts) classified as having an average particle size of 100% 22 microns and finer, 97% 11 microns and finer ($CaCO_3$, 0.4% by weight as $CO_2$) was slurried in 280 parts deionized water containing 6 parts of alkylaryl polyoxy carboxylate surfactant, and screened through 325 mesh to break up any reagglomerated particles of calcium hydroxide.

One half of the melted stearic acid at 160° F. and one half of the calcium hydroxide slurry were mixed together all at once with stirring, and reacted immediately. The remaining stearic acid and slurry were added and steam at 45 psi supplied to the reactor jacket. After 20 minutes a solution of 5.5 parts acetic acid in 150 parts water was added. Mixing at temperature continued for a total of 5 hours with periodic sampling to follow the progress of the reaction by the reduction in free fatty acid content.

The resulting calcium stearate—calcium acetate product melted in the range from 150° to 157° C. (Fischer-Johns block), analyzed 0.55% free fatty acid, 9.5% calcium oxide ash, and gave an acceptable pressure pack test.

The results show the successful preparation of a calcium stearate—calcium acetate product with properties indicating its suitability for use in polyolefin plastics.

EXAMPLE 2

A steam-jacketed sigma blade mixer was charged with 1200 parts melted commercial stearic acid at 160° F., 2 parts alkylaryl polyoxy carboxylate surfactant, and 50 grams deionized water. With the jacket empty, 166 parts calcium hydroxide (classified as in Example 1) was added through a vibrating 14 mesh screen within 10 minutes. Additional 80 parts deionized water was added, the mixer closed and steam at 18 psi supplied to the jacket.

After 2½ hours of mixing at 40 rpm, the batch analyzed 0.54% free fatty acid and gave a hazy hydrocarbon solution. A solution of 5 parts acetic acid in 50 parts deionized water was added and mixing was continued for a total of 5½ hours, and the product discharged. The resulting calcium stearate—calcium acetate product melted at 147°–151° C., analyzed 0.45% free fatty acid, 9.43% calcium oxide ash, and gave a hydrocarbon solution with only slight haze.

The results show the successful preparation of a calcium stearate—calcium product with properties indicating its suitability for use in polyolefin plastics.

EXAMPLE 3

A high speed mixer was charged with a mixture of 1200 parts commercial stearic acid (molecular weight 276), 80 parts deionized water, and 2 parts alkylaryl polyoxy carboxylate surfactant at 160° F. Agitation was started at 90 rpm, and 164.5 parts fine calcium hydroxide (classified as in Example 1) was added during 5 minutes, followed by 80 parts deionized water. The reactor was closed and mixed for 1½ hours with steam at 15 psi in the jacket.

After 1½ hours, a solution of 1 part acetic acid in 40 parts water was added, and mixing continued. After a total of 3½ hours, analysis of the resulting product showed melting point 147°–151° C., apparent density 16 pounds per cubic foot, 0.55% free fatty acid and 9.32% calcium oxide ash, 0.01% water soluble salts (as sodium chloride), 95% transmission at 650 nm for a 3% decalin solution at 130° C., and a very low pressure buildup for the screen pack test.

The results show the successful preparation of a calcium stearate acetate product with properties indicating its suitability for use in polyolefin plastics.

EXAMPLE 4

The same reactor as in Example 3 was charged with a mixture of 1200 parts commercial stearic acid (molecular weight 276), 50 parts deionized water, and 2 parts alkylaryl polyoxy carboxylate surfactant at 160° F. Agitation was started at 90 rpm, and 164.5 grams calcium hydroxide classified as in Example 1 was added during 5 minutes. The reactor was closed and mixed for 3 hours with steam at 15 psi in the jacket.

A solubility test showed the product would be soluble in decalin with only a very slight haze. Analysis of the ground product after removal from the reactor showed melting point 147°–150° C., 0.55% free fatty acid and 9.33% calcium oxide ash.

The results show the successful preparation of a calcium stearate product with properties indicating its suitability for use in polyolefin plastics.

EXAMPLE 5

A steam-jacketed sigma blade mixer was charged with 1164 parts melted commercial stearic acid, and 36 grams of glyceryl tristearate at 140° F.; 163 parts fine calcium hydroxide (classified as in Example 1), 1.6 parts alkylaryl polyoxy carboxylate surfactant, 230 parts deionized water was added. Steam at 10 psi was supplied to the jacket. After 4 hours mixing with the reactor closed, 300 parts water was added and mixing continued for one hour with the reactor closed and one half hour of subsequent drying.

The product was discharged and showed softening at 133° C. and melting point 147°–149° C., free fatty acid content 0.4%, and calcium oxide ash 9.3%.

The results show the successful preparation of a calcium stearate—glyceryl tristearate product with properties indicating its suitability for use in polyolefin plastics.

EXAMPLE 6

A jacketed reactor was charged with 500 parts by weight of melted commercial stearic acid and 16 parts by weight of water, and cooling water was supplied to the jacket. With the reactor contents at 136° F., 75 parts fine calcium hydroxide (classified as in Example 1) was added. Reaction was instantaneous. After five minutes, a second charge of 500 parts stearic acid, 16 parts water, and 75 parts fine calcium hydroxide was made, and after a further five minutes a third charge of 200 parts of stearic acid and 40 parts of fine calcium hydroxide was made. Steam was supplied to the jacket for one half hour, followed by cooling water.

The calcium stearate product was ground and screened to remove 106 parts by weight (less than 8%) of oversize greater then 20 mesh and afford the remainder with 100% passing 20 mesh, 36% passing 200 mesh, and 13% passing 325 mesh. This ground and screened material had apparent density of 23 pounds per cubic foot, analyzed 0.47% free fatty acid and 10.6% calcium oxide ash, and was soft and free of grit. Filtration of a hot hydrocarbon solution through a 325 mesh screen showed 0.021% residue.

The results show the preparation in accordance with this invention of a calcium stearate product suitable for knife blade coating of base stocks with PVC solution coatings containing calcium stearate.

COMPARISON EXAMPLE A

A reactor with high speed agitator was charged with a mixture of 1200 parts commercial stearic acid (molecular weight 276), 80 parts deionized water, and 2 parts alkylaryl polyoxy carboxylate surfactant at 160° F. Agitation was started at 90 rpm. Instead of 164.5 parts fine calcium hydroxide, there was added during 5 minutes 164.5 parts of a calcium hydroxide having 2% particles larger than 45 microns.

This was followed by 80 parts deionized water. The reactor was closed and mixed for ½ hours with steam at 15 psi in the jacket.

After 1½ hours, a solution of 1 gram acetic acid in 40 grams water was added, and mixing continued. After a total of 3½ hours analysis of the resulting product showed 0.5% free fatty acid and 9.5% calcium oxide ash.

The conditions of this Comparison Example A are identical to those of Example 3 except for the use of a calcium hydroxide reactant with a significant content of particles greater than 11 microns (more than 22% compared to 3%). The resulting calcium stearate—calcium acetate product failed with filterability test and consequently manifested properties indicating that it would not pass a pressure pact test suitable for use in polyolefin plastics. The results also show that the use of calcium hydroxide containing 100% particles less than 22 microns at least 97% particles of particle size not greater than 11 microns in accordance with this invention is critical to success in this critical application.

COMPARISON EXAMPLE B

A jacketed reactor was charged with 500 parts by weight of melted commercial stearic acid and 16 parts by weight of water, and cooling water was supplied to the jacket. With the reactor contents at 136° F., 75 parts of the same calcium hydroxide used in Comparison Example A was added. Reaction occurred after some delay. After five minutes, a second charge of 500 parts stearic acid, 16 parts water, and 75 parts of the same calcium hydroxide was made, and after a further five minutes a third change of 200 parts of stearic acid and 40 parts of the same calcium hydroxide. Steam was supplied to the jacket for one half hour, followed by cooling water to powder out the batch.

The calcium stearate product was ground and screened to remove 109 parts by weight (approximately 8%) of oversize greater than 20 mesh and afford the remainder with 100% passing 20 mesh, 36% passing 200 mesh, and 13% passing 325 mesh. This ground and screened material analyzed 0.73% free fatty acid and 11.03% calcium oxide, and contained noticeable quantities of grit. 0.16 percent by weight of the material dissolved in hydrocarbon blocked a 325 mesh (45 micron) screen.

The results show that the use of calcium hydroxide with particle size not exceeding 22 microns in accordance with this invention is critical to success in obtaining a calcium stearate substantially free of grit.

We claim:

1. A process for manufacturing a calcium salt of an aliphatic carboxylic acid, substantially free of excess calcium hydroxide, having twelve to twenty-two carbon atoms comprising the steps of (1) conveying into a mixing zone at least one aliphatic carboxylic acid having twelve to twenty-two carbon atoms and a calcium hydroxide product having a maximum particle size of 22 microns wherein the proportions of carboxylic acid to calcium hydroxide are in the range of 1.8 to 2.2 moles of carboxylic acid per mole of calcium hydroxide, (2) applying heat as necessary, (3) mixing until the reaction has progressed to the desired end point, and (4) discharging calcium carboxylate salt substantially free of excess calcium hydroxide from the mixing zone.

2. A process according to claim 1 in which said carboxylic acid is selected from the group consisting of saturated straight chain aliphatic acids.

3. A process according to claim 1 in which said carboxylic acid comprises commercial stearic acid.

4. A process according to claim 1 in which said carboxylic acid is lauric acid.

5. A process according to claim 1 in which said carboxylic acid is behenic acid.

6. A process according to claim 1 in which the calcium hydroxide contains at least 97% of particles having a maximum particle size of 11 microns.

7. A process according to claim 1 in which the calcium hydroxide product contains calcium carbonate and said calcium carbonate comprises no more than 1.36% by weight of said product.

8. A process according to claim 1 in which the temperature is maintained within a range of 50° to 110° C.

9. A process according to claim 1 in which mixing is at a rate of 40 to 150 rpm.

10. A process according to claim 1 in which the proportions of carboxylic acid to calcium hydroxide are in the range of 1.96 to 2.01 moles of carboxylic acid per mole of calcium hydroxide.

11. A process according to claim 3 in which the proportions of calcium hydroxide, are in the range from 13 to 17 parts by weight of calcium hydroxide per 100 parts by weight of stearic acid.

12. A process according to claim 3 in which water in a proportion of 2 to 10 parts by weight per 100 parts by weight of stearic acid is conveyed into the mixing zone.

13. A calcium stearate substantially free of grit manufactured by a process according to claim 3.

14. A composition comprising:

a directly neutralized calcium stearate substantially free of excess calcium hydroxide, characterized by a melting point in the range from 131° to 159° C., an ash content in the range from 9% to 12% by weight as calcium oxide, a free fatty acid content not exceeding 1% by weight, a water soluble salt content in the range from 0.001% to 0.1% by weight, and an apparent density in the range from 15 to 25 pounds pet cubic foot; and calcium acetate in which the molar proportions of calcium acetate to calcium stearate range from 1:18 to 1:280.

15. A calcium stearate according to claim 14 whose percent transmission at 650 nm of a 3% solution in decalin at 130° C. is at least 90%.

16. A calcium stearate according to claim 14 in which the content of free fatty acid does not exceed 0.5% by weight.

17. A calcium stearate according to claim 15 in which the water soluble salt content does not exceed 0.03%.

18. A composition according to claim 14 in which the molar proportions of calcium acetate to calcium stearate range from 1:80 to 1:170.

19. A composition comprising:

a directly neutralized calcium stearate substantially free of excess calcium hydroxide, characterized by a melting point in the range from 131° to 159° C., an ash content in the range from 9% to 12% by weight as calcium oxide, a free fatty acid content not exceeding 1% by weight as calcium oxide, a free fatty acid content not exceeding 1% by weight, a water soluble salt content in the range from 0.001% to 0.1% by weight, and an apparent density in the range from 15 to 25 pounds per cubic foot; and a saturated triglyceride in which the proportions by weight by triglyceride to calcium stearate range from 4:96 to 1:99 and the free fatty acid content does not exceed 0.5% weight.

20. A composition according to claim 19 whose percent transmission at 650 nm of a 3% solution in decalin at 130° C. is at least 90%.

21. A composition according to claim 19 in which the content of free fatty acid does not exceed 0.5% by weight.

22. A composition according to claim 19 in which the water soluble salt content does not exceed 0.03%.

23. A composition according to claim 19 in which the triglyceride is glyceryl tristearate.

* * * * *